US008939939B2

(12) United States Patent
Funamura et al.

(10) Patent No.: US 8,939,939 B2
(45) Date of Patent: Jan. 27, 2015

(54) FISTULA CATHETER

(75) Inventors: Shigeaki Funamura, Fukuroi (JP); Motonori Watanabe, Fukuroi (JP)

(73) Assignee: Covidien LP, Mansfield, MA (US)

( * ) Notice: Subject to any disclaimer, the term of this patent is extended or adjusted under 35 U.S.C. 154(b) by 496 days.

(21) Appl. No.: 13/246,411

(22) Filed: Sep. 27, 2011

(65) Prior Publication Data

US 2012/0078192 A1 Mar. 29, 2012

(30) Foreign Application Priority Data

Sep. 28, 2010 (JP) ................................ 2010-217326

(51) Int. Cl.
*A61M 5/32* (2006.01)
*A61J 15/00* (2006.01)

(52) U.S. Cl.
CPC .......... *A61J 15/0015* (2013.01); *A61J 15/0034* (2013.01); *A61J 15/0061* (2013.01); *A61J 15/0065* (2013.01); *A61J 15/0038* (2013.01)
USPC ........................................................ 604/175

(58) Field of Classification Search
CPC ..... A61J 15/00; A61J 15/0015; A61J 15/003; A61J 15/0034; A61J 15/0042; A61J 15/0049; A61J 15/0057; A61J 15/0061; A61J 15/0065; A61J 15/0069; A61M 2039/0255; A61M 2039/0261
USPC ........................................ 604/174, 175, 910
See application file for complete search history.

(56) References Cited

U.S. PATENT DOCUMENTS 2,687,131 A 8/1954 Raiche
3,509,884 A 5/1970 Bell
4,850,953 A 7/1989 Haber et al.
5,267,968 A * 12/1993 Russo .......................... 604/174
5,269,770 A 12/1993 Conway et al.
5,374,254 A * 12/1994 Buma .......................... 604/175
5,399,173 A 3/1995 Parks et al.
5,656,013 A 8/1997 Yoon
5,836,924 A 11/1998 Kelliher et al.

(Continued)

FOREIGN PATENT DOCUMENTS

EP 2119424 A2 11/2009

OTHER PUBLICATIONS

Australian Examination Report dated Aug. 6, 2012 in copending Australian Appln. No. 2011232763.

(Continued)

*Primary Examiner* — Kami A Bosworth
*Assistant Examiner* — Glen Janson

(57) ABSTRACT

A fistula catheter which allows a supply tube to be easily connected to a body-external fixing member positioned on the body surface side, and which is only slightly invasive for a patient is provided. The fistula catheter 10 includes a tube body 11 which is inserted into a fistula formed in the abdominal wall and the wall of the alimentary canal; a body-external fixing part 12 which is linked to one end of the tube body 11 and positioned on the abdominal wall surface side of the fistula; and a body-internal fixing part 13 which is linked to the other end of the tube body 11 and positioned inside the wall of the alimentary canal. The body-internal fixing part 13, and the fistula catheter has a flow path allowing fluid to flow through the body-external and body-internal fixing members. The body-external fixing part 12 includes a flexible tube 1 and is connected substantially at right-angles to the axial direction of the tube body 11.

7 Claims, 7 Drawing Sheets

(56) References Cited

U.S. PATENT DOCUMENTS

| | | | | |
|---|---|---|---|---|
| 5,865,816 | A | 2/1999 | Quinn | |
| 5,910,128 | A * | 6/1999 | Quinn | 604/93.01 |
| 6,102,928 | A | 8/2000 | Bonutti | |
| 6,458,106 | B1 * | 10/2002 | Meier et al. | 604/264 |
| 6,482,183 | B1 | 11/2002 | Pausch et al. | |
| 6,546,280 | B2 | 4/2003 | Osborne | |
| 2002/0177806 | A1 * | 11/2002 | Meier et al. | 604/104 |
| 2002/0193753 | A1 | 12/2002 | Rouns et al. | |
| 2003/0216713 | A1 * | 11/2003 | Kessler et al. | 604/533 |
| 2008/0082081 | A1 * | 4/2008 | Melsheimer | 604/523 |
| 2008/0312640 | A1 * | 12/2008 | Grant | 604/533 |

OTHER PUBLICATIONS

European Search Report dated Feb. 4, 2014 in European Appln. No. EP 11 00 7849.

* cited by examiner (a)

(b)

(a)

(b)

(c)

FISTULA CATHETER

TECHNICAL FIELD

The present disclosure relates to a fistula catheter which is used to supply fluids such as liquid food or nutrients into a patient's alimentary canal.

BACKGROUND

It is conventional practice to make use of a fistula catheter in order to administer enteral feeding for supplying liquid food or nutrients etc. to persons (referred to hereinafter as "patient(s)") who have a reduced capacity to ingest food orally under their own power, due to advanced age or illness. When enteral feeding is administered, a fistula (gastric fistula) is established in the patient's abdomen region, a fistula catheter is fitted into the fistula, and liquid food etc. is supplied to the patient through the fistula catheter.

Fistula catheters which are used for administering enteral feeding can be broadly divided into what are known as tube-type and button-type according to the shape of the body-external fixing member which is disposed on the body surface. Tube-type fistula catheters have a longer tube on the body surface side than button-type fistula catheters, and therefore it is a simple matter to connect this tube with a supply tube connected to a nutrient bag containing nutrients etc. However, the long tube of a fistula catheter remains permanently on the patient's body surface, and therefore the tube may form a bulge under clothing, which is unattractive, or the tube may obstruct operations.

Many patients prefer button-type fistula catheters in which the member disposed on the body surface side is smaller than that of tube-type fistula catheters. A button-type fistula catheter of this kind which has been proposed may comprise a tube extending along the wall surface of a fistula and having an internal nutrient passage for introducing nutrients or drug solutions into the stomach from outside the body; a non-balloon-type body-internal indwelling part which is made indwelling inside the stomach in an embedded state in the body, which projects with an enlarged diameter radially outward of the tube and which is attached to the tip end of the tube, the diameter of the non-balloon-type body-internal indwelling part being reduced from the projecting state under the action of an external force applied by an obturator; and a body-external fixing part which projects in the radial direction of the tube and is attached to the rear end of the tube. See, for example, Japanese Unexamined Patent Application Publication No. 2006-35001.

With a button-type fistula catheter such as disclosed above, a supply tube connected to a nutrient bag or the like is connected to a body-external fixing member which is positioned on the body surface, and nutrients etc. are administered. The body-external fixing part is positioned close to the body surface, and therefore it is difficult to connect the supply tube if the body-external fixing member is small. If the body-external fixing member is large, on the other hand, there is a strong possibility that it will touch the patient's body surface, which is intrusive. If clothing etc. touches the supply tube, particularly while the supply tube connected to the nutrient bag or the like is in a state of connection, there is a possibility that the body-external fixing member will also be tilted as the supply tube is touched, and will partially bite into the patient's body surface; this leads to the risk of damaging the fistula and causing the patient pain.

Furthermore, when a button-type fistula catheter has been put in place and is then replaced with a tube-type fistula catheter, the tube-type fistula catheter has to be attached once the button-type fistula catheter has been withdrawn, which is invasive for the patient and risks leading to serious complications.

The present disclosure has been devised in order to resolve the kind of issues outlined above, and the object of the disclosure lies in providing a fistula catheter which allows the supply tube to be easily connected to the body-external fixing member positioned on the body surface side, and which is only slightly invasive for the patient.

SUMMARY

The fistula catheter according to the present disclosure can comprise: a tube body which is inserted into a fistula formed in the abdominal wall and the wall of the alimentary canal; a body-external fixing member which is linked to one end of the tube body and positioned on the abdominal wall surface side of the fistula; and a body-internal fixing member which is linked to the other end of the tube body and positioned inside the wall of the alimentary canal; wherein the abdominal wall and the wall of the alimentary canal are held by the body-external fixing member and the body-internal fixing member, and the fistula catheter has a flow path allowing fluid to flow therethrough; the body-external fixing member includes a flexible tube member and is connected substantially at right-angles to the axial direction of the tube body; and a pulling-restriction member which extends in a different direction to the direction of connection of the body-external fixing member to the tube body is provided on at least part of the tube body and the body-external fixing member. In accordance with one or more aspects of the invention, a fistula catheter for insertion into a fistula can comprise a tube body configured to be disposed in the fistula, wherein the tube body typically has a first end and a second end that is opposite the first end, wherein the tube body typically defines a flow path from the first end to the second end; a body-internal fixing part connected to the second end of the tube body; a body-external fixing part linked to the first end of the tube body, wherein the body-external fixing part typically has a body-external-fixing-part axis that is orthogonal to an axis of the flow path of the tube body; and a pulling-restriction member attached to the body-external fixing part. The pulling-restriction member can be comprised of a bendable tube secured to the body-external fixing part, wherein the bendable tube has an axis that is orthogonal the flow path of the tube body. The pulling-restriction member can be comprised of a projection in the opposite direction to a connection direction of the body-external fixing part. The body-internal fixing part can comprise one of a tube with a helical shape, an expandable hemispherical member, and an expandable balloon. The tube body and the body-external fixing part can be formed as a single tube. The pulling-restriction member can be, in some cases, a dish-like outer shape comprised of a flexible material.

In the fistula catheter according to the present disclosure, a connector for can detachably connect a fluid supply tube which supplies fluid is provided at one end of the body-external fixing member on the opposite side to the side which is connected to the tube body.

The connector of the fistula catheter according to the present disclosure can comprise: a lock ring which comprises, on its inner peripheral surface, a thread part that screws together with a thread provided on the fluid supply tube; and a cylindrical member which has a larger diameter than the outer diameter of the lock ring and is provided adjacent to the lock ring and substantially coaxially with the lock ring.

The pulling-restriction member of the fistula catheter according to the present disclosure can include a flexible member which can be placed over the body-external fixing member by being bent.

The body-external fixing member and the tube body of the fistula catheter according to the present disclosure can be formed by a single tube member.

The body-external fixing member of the fistula catheter according to the present disclosure can be formed by a flexible tube member and can be connected substantially at right-angles to the axial direction of the tube body. This means that when the fistula catheter is fitted in the patient's fistula, the body-external fixing member can be positioned running along the body surface. The body-external fixing member positioned on the body surface is therefore unlikely to obstruct patient activity and it can be easily connected to the tube for supplying nutrients etc. Furthermore, the body-external fixing member can include a tube member, and therefore it is unlikely to cause the patient any pain, and is only slightly invasive. Furthermore, the pulling-restriction member is provided, so it is possible to prevent the fistula catheter from being pulled into the fistula when the fistula catheter is fitted in the fistula.

Furthermore, a connector for detachably connecting a fluid supply tube which supplies fluid can be provided at one end of the body-external fixing member on the opposite side to the side which is connected to the tube body. This means that the fistula catheter according to the present disclosure can be used as what is known as a button-type fistula catheter, and by connecting the tube for supplying nutrients etc. to the connector, it can be used as what is known as a tube-type fistula catheter.

Furthermore, the connector of the fistula catheter according to the present disclosure can comprise: a lock ring which comprises, on its inner peripheral surface, a thread part that screws together with a thread provided on the fluid supply tube; and a cylindrical member which has a larger diameter than the outer diameter of the lock ring and is provided adjacent to the lock ring and substantially coaxially with the lock ring. This means that it is possible to prevent the supply tube etc. from being inadvertently detached from the connector.

Furthermore, the pulling-restriction member of the fistula catheter can include a flexible member which can be placed over the body-external fixing member by being bent, and therefore it is simple to press the body-external fixing member in order to block the flow path thereof by pinching the body-external fixing member along with the pulling-restriction member.

Furthermore, the body-external fixing member and the tube body of the fistula catheter according to the present disclosure can be formed by a single tube member, and therefore it is possible to reduce the number of components and to reduce production costs.

BRIEF DESCRIPTION OF THE DRAWINGS

Various exemplary embodiments of the presently disclosed fistula catheter will be described herein with reference to the accompanying drawings, wherein.

DETAILED DESCRIPTION

Mode of Embodiment 1

Figure 1:
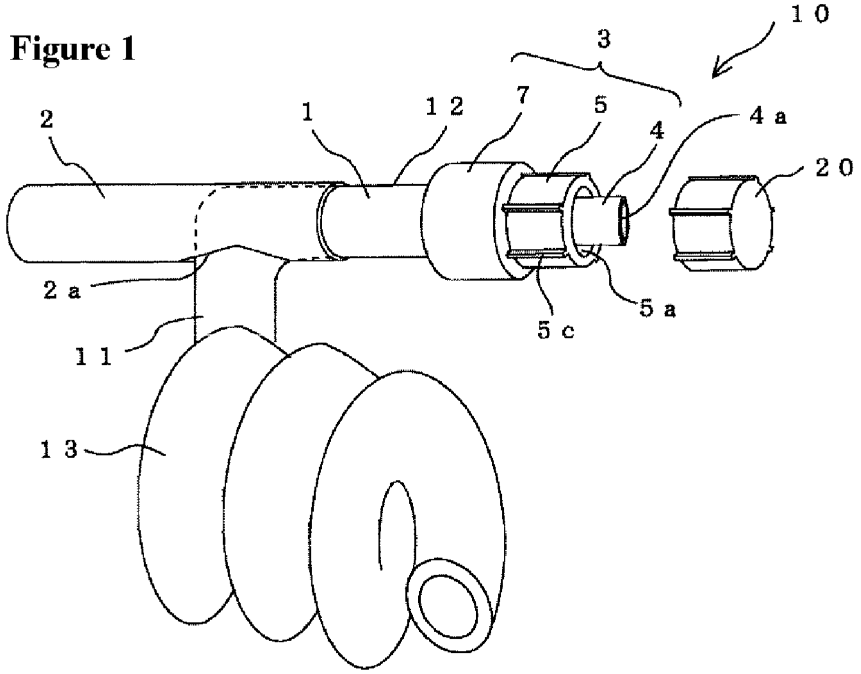
FIG. 1 is an oblique view of the fistula catheter according to Mode of Embodiment 1.
Figure 2:
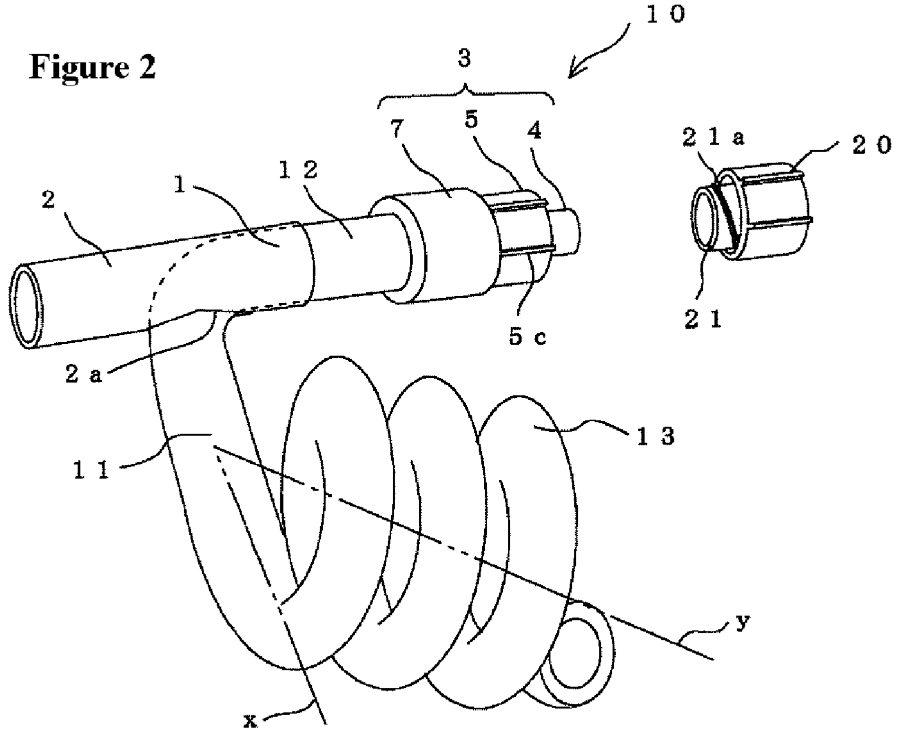
FIG. 2 is an oblique view seen from another direction of the fistula catheter according to Mode of Embodiment 1.
Figure 3:
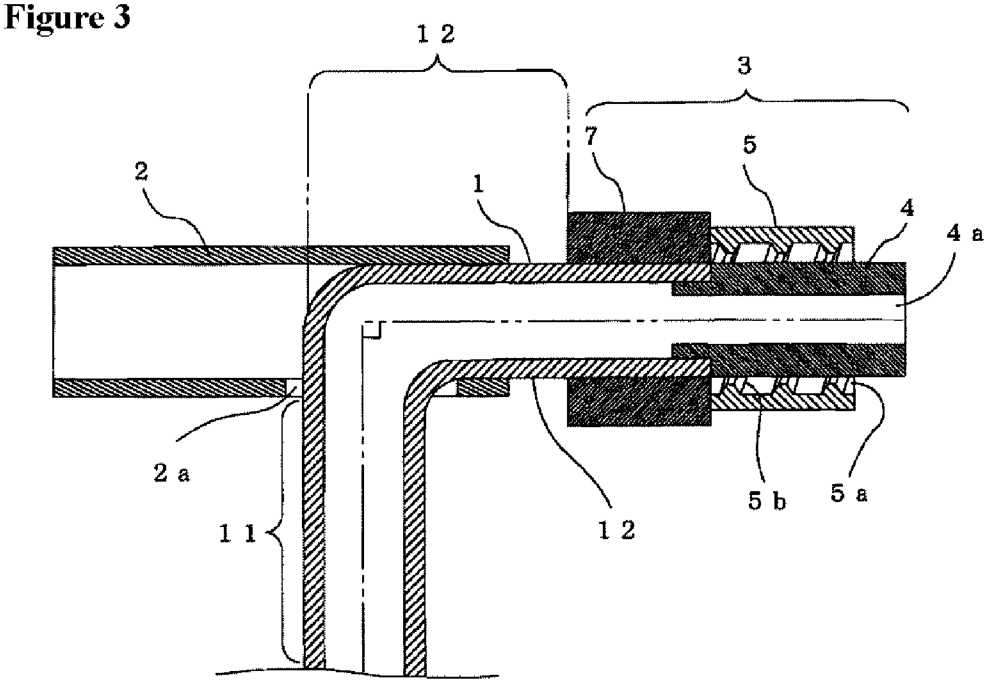
FIG. 3 is a schematic view in cross section of the main parts of the fistula catheter according to Mode of Embodiment 1.
Figure 4:
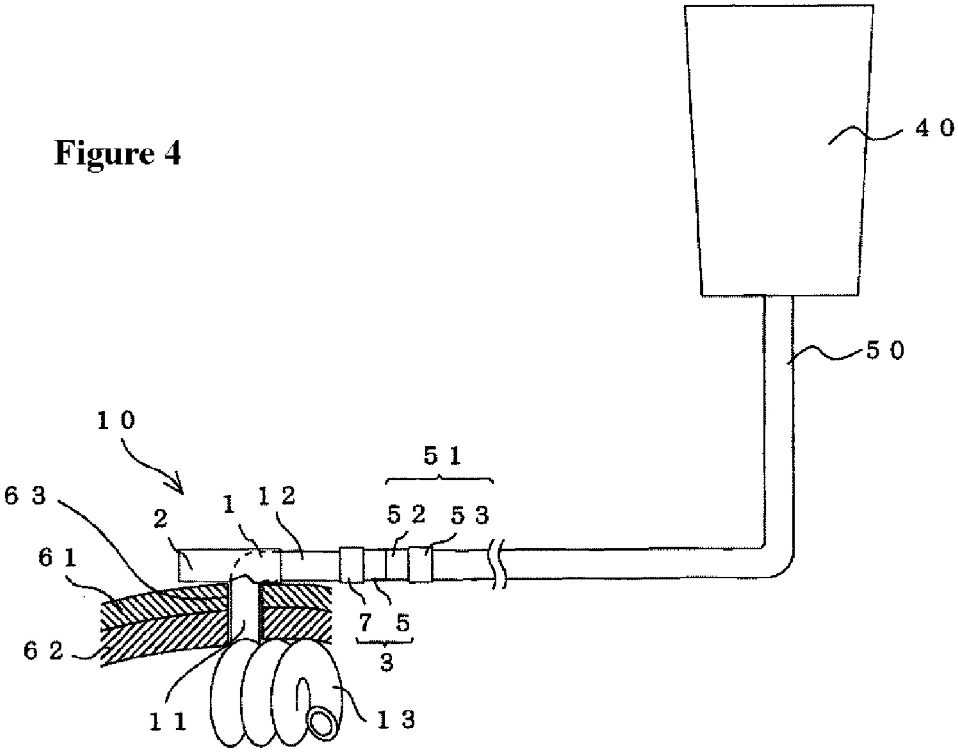
FIG. 4 is a general view showing fluid being supplied using the fistula catheter according to Mode of Embodiment 1.

FIG. 1 is an oblique view of a fistula catheter 10 according to Mode of Embodiment 1; FIG. 2 is an oblique view seen from another direction of the same fistula catheter 10; and FIG. 3 is a schematic view in cross section of the main parts of the same fistula catheter 10. FIG. 4 is a general view showing fluid being supplied to a patient using the fistula catheter 10 according to Mode of Embodiment 1. In the following description, for the sake of convenience, the upper side of the drawing in FIG. 3 will be described as the upper side of the fistula catheter 10 and the lower side of the drawing in FIG. 3 will be described as the lower side of the fistula catheter 10. It should be noted that in the figures, the size relationships among the members may differ from the actual size relationships.

As shown in FIG. 4, the fistula catheter 10 is fitted in a fistula 63 which is formed in the abdominal wall 61 and the wall of the alimentary canal (the stomach wall 62 or the intestinal wall etc.), and it is used to supply a fluid such as liquid food or nutrients contained in a nutrient bag 40 to the stomach or intestines of a patient through a supply tube 50. The fistula catheter 10 and the supply tube 50 are connected to each other by linking a connector member 3 provided on the fistula catheter 10 with a connector member 51 provided on the supply tube 50.

As shown in FIGS. 1 to 4, the fistula catheter 10 comprises: a tube 1; a pulling-restriction member 2; and the connector member 3 which connects the supply tube 50 and the fistula catheter 10. Furthermore, in Mode of Embodiment 1, a tube body 11 which is inserted into the fistula 63, a body-external fixing part 12 and a body-internal fixing part 13 are formed by a single tube 1. Furthermore, a cap 20 (FIG. 2) is attached to the connector member 3 when the supply tube 50 is not connected.

In one embodiment, the tube 1 is made of a resin material such as polyurethane resin, vinyl chloride resin, silicone resin, polypropylene resin or polyethylene resin, for example, and it has an internal cavity allowing the passage of the fluid. The material of the tube 1 is not limited to the materials mentioned above, but the tube 1 is preferably made of a material which is sufficiently soft and flexible that it can be pressed or bent by the patient or practitioner in order to block the flow path of the tube 1, as will be described later. It should be noted that the inside of the tube 1 is hollow and a check valve or similar is not provided therein, for example. The body-external fixing part 12, tube body 11 and body-internal fixing part 13 which are formed by the single hollow tube 1 therefore allow a fluid such as nutrients to flow therethrough.

The body-external fixing part 12 can be produced by thermoforming in a state in which the tube 1 is bent at substantially right-angles to the axial direction of the tube body 11. The body-external fixing part 12 holds the wall of the alimentary canal, such as the stomach wall, and the abdominal wall between itself and the body-internal fixing part 13 when the fistula catheter 10 is fitted in the fistula (see FIGS. 4 and 7). The body-external fixing part 12 is substantially at right-angles to the tube body 11 which is inserted into the fistula, and therefore it has the function of inhibiting pulling of the fistula catheter 10 into the fistula. There is no particular limitation as to the length of the body-external fixing part 12, but it may be around 2-7 cm, for example. It should be noted that Mode of Embodiment 1 and the subsequent modes of embodiment describe an example in which the tube 1 is bent in order to form the tube body 11 and the body-external fixing part 12, but the method for connecting the tube body 11 and the body-external fixing part 12 is not limited to this method. For example, the tube body 11 and the body-external fixing part 12 may be connected substantially at right-angles by way of a joining member such as a coupling, or the corresponding ends of the tube body 11 and the body-external fixing part 12 may be heat-sealed in order to connect the two substantially at right-angles.

The body-internal fixing part 13 is joined to the lower part of the tube body 11 and is formed by setting the tube 1 in a helical shape. The body-internal fixing part 13 is set in such a way that the centre axis x of the tube body 11 (the long axis of the tube body 11; see FIG. 2) and the centre y of the helical shape (the imaginary axis passing through the centre of the helical shape of the body-internal fixing part 13; see FIG. 3) are at approximately 45°.

The connector member 3 comprises: a cylindrical connector body 4 which is connected to the end of the tube 1 on the body-external fixing part 12 side; a lock ring 5; and a cylindrical member 7.

The connector body 4 has an internal cavity 4*a* which forms a fluid flow path. Furthermore, the rear end of the connector body 4 (the end positioned on the tube 1 side) has a reduced diameter and is inserted into the internal cavity of the tube 1 in a liquid-tight state.

The lock ring 5 is formed as a substantially cylindrical shape and is of a size which can internally receive the connector body 4 with a gap 5*a* therebetween. That is to say, the lock ring 5 is set to a size which allows the connecting part of a connector 52 of the supply tube 50 to be inserted into the gap 5*a* (i.e., between the inner peripheral surface of the lock ring 5 and the connector body 4). The lock ring 5 is designed to be rotatable in the circumferential direction, and is also designed to be mobile in the axial direction of the connector body 4.

A female thread 5*b* is formed in the lock ring 5 from the tip end up to the base end of the inner peripheral surface thereof. The female thread 5*b* is formed so as to be able to screw together with a male thread (not depicted) which is formed on the connector member 51 of the supply tube 50 or the cap 20. Furthermore, anti-slip protrusions 5*c* which extend in the axial direction are formed at prescribed intervals in the circumferential direction on the outer peripheral surface of the lock ring 5. It should be noted that the connector body 4 and the lock ring 5 may be made of polycarbonate, for example.

The cylindrical member 7 is a tubular member which has a larger external shape than the external shape of the lock ring 5. The cylindrical member 7 is disposed in such a way as to be coaxial with the lock ring 5 and adjacent to the lock ring 5 on the body-external fixing part 12 side.

The pulling-restriction member 2 is a member which serves to prevent the fistula catheter 10 from being pulled into the fistula when the fistula catheter 10 is fitted in the patient's fistula, and the member is positioned on the surface side of the abdominal wall when it is fitted to the fistula. In Mode of Embodiment 1, the pulling-restriction member 2 is provided in such a way as to project in the opposite direction to the connection direction of the body-external fixing part 12 to the tube body 11. Furthermore, the pulling-restriction member 2 includes a hollow member made of a soft and flexible material. The body-external fixing part 12 of the tube 1 is inserted through the pulling-restriction member 2 from a hole 2*a* provided midway along the hollow member towards one end of the hollow member, whereby the pulling-restriction member 2 is attached to the body-external fixing part 12. As shown in FIGS. 1 to 3, the pulling-restriction member 2 and the body-external fixing part 12 have a substantially linear shape, while the tube body 11 extends downwards from a position substantially at the midpoint of the two so that a "T"-shape is formed overall.

The cap 20 is used to prevent the return flow of fluid, such as fluid inside the stomach, from the connector body 4 on the surface side when the supply pipe 50 is not connected to the fistula catheter 10, the cap being connected to the connector body 4 of the connector member 3. A cylindrical connecting part 21 is provided on the cap 20, and a male thread 21*a* which can screw together with the female thread 5*b* of the lock ring 5 is formed on the outer peripheral surface of the connecting part 21.

As shown in FIG. 4, the connector member 51 for connecting with the connector member 3 of the fistula catheter 10 is provided at the tip end of the supply tube 50. The connector member 51 is provided with a connector 52 having at least a cylindrical connecting part which can be inserted into the gap 5*a* of the lock ring 5, and a male thread which can screw together with the female thread 5*b* of the lock ring 5 and is provided on the outer peripheral surface of the connecting part. The connector member 51 in Mode of Embodiment 1 is also provided with a cylindrical member 53 having the same structure as the cylindrical member 7.

Figure 5:
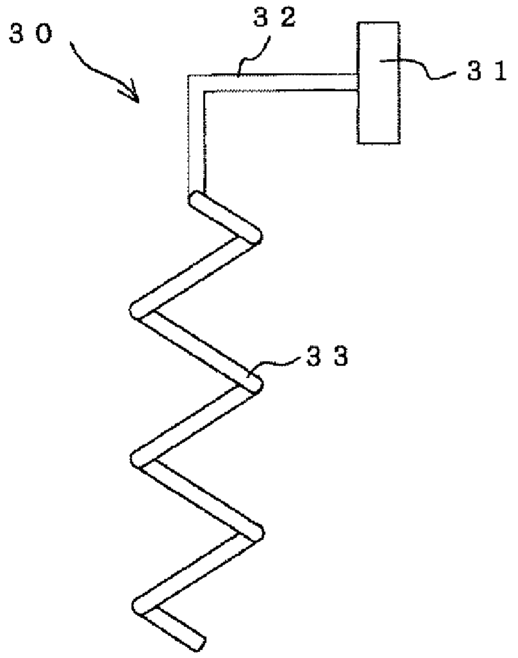
FIG. 5 illustrates an extension tool which is used when the fistula catheter according to Mode of Embodiment 1 is fitted in the patient's fistula.

FIG. 5 shows an extension tool 30 which is used when the fistula catheter 10 is fitted in the fistula. The extension tool 30 is made of a material which is harder than that of the tube 1 of the fistula catheter 10, for example a resin such as polypropylene, polyurethane, silicone, polycarbonate, polyethylene or nylon, or a metal such as stainless steel. The extension tool 30 comprises: a grip part 31 extending in a vertical direction; a straight rod-like horizontal part 32 extending from substantially the centre of the grip part 31 in a horizontal direction; and a helical rod-like insertion part 33 extending from the end of the horizontal part 32. The surfaces of the horizontal part 32 and the insertion part 33 are coated with silicone or surface-textured so that it is possible to improve the ease of insertion when inserted into the tube 1 of the fistula catheter 10. Furthermore, the horizontal part 32 and the insertion part 33 are formed to a degree of thickness which allows them to pass through the internal cavity of the tube 1, and the helical shape of the insertion part 33 is formed in such a way that the diametric direction thereof is shorter and the axial direction is longer than the helical shape of the body-internal fixing part 13.

Figure 6:
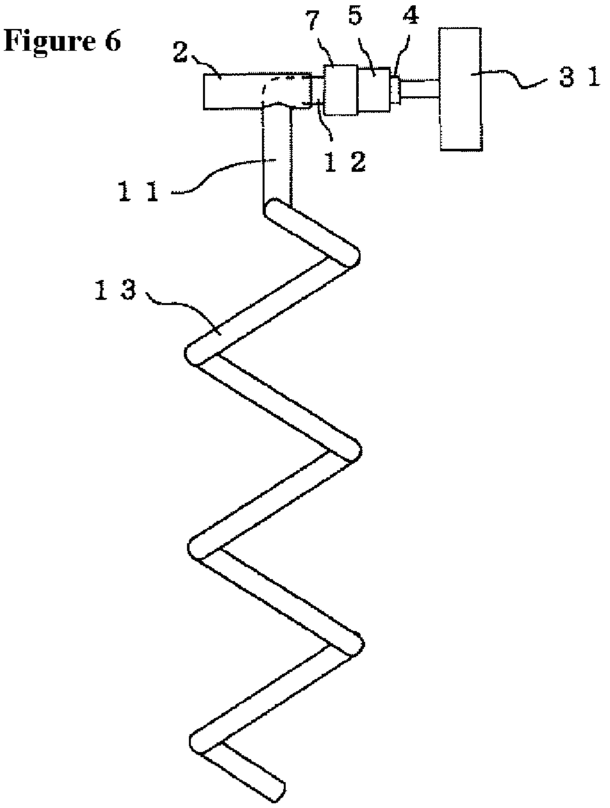
FIG. 6 shows the situation when the extension tool is fitted to the fistula catheter according to Mode of Embodiment 1.

FIG. 6 shows the situation when the extension tool 30 having the structure described above is inserted into the fistula catheter 10. When the insertion part 33 of the extension tool 30 is inserted from the connector member 3 and introduced into the tube 1, the body-internal fixing part 13 of the fistula catheter 10 forms a helical shape which follows the shape of the insertion part 33 of the extension tool 30, as shown in FIG. 6. When the insertion part 33 of the extension tool 30 is inserted into the fistula catheter 10, the insertion part 33 of the extension tool 30 is easily inserted into the fistula catheter 10 by pushing while rotating the extension tool 30 with respect to the fistula catheter 10. Furthermore, when the extension tool 30 is removed from the fistula catheter 10, the extension tool 30 is easily removed from the fistula catheter 10 by pulling while rotating the extension tool 30 in the opposite direction to the abovementioned direction of rotation with respect to the fistula catheter 10.

It should be noted that in Mode of Embodiment 1, the example described relates to the extension tool 30 which comprises the horizontal part 32 extending from the grip part 31 and the helical rod-like insertion part 33, but the shape of the extension tool is not limited to the abovementioned shape. For example, the straight horizontal part 32 extending from the grip part 31 may be extended to form a "T"-shaped extension tool which is not provided with the helical rod-like insertion part 33. The tube body 11, body-external fixing part 12 and body-internal fixing part 13 are formed by the flexible tube 1, and therefore it is possible to insert a straight extension tool, and the tube 1 is able to return to its original shape when the extension tool is removed from the fistula catheter 10.

Figure 7:
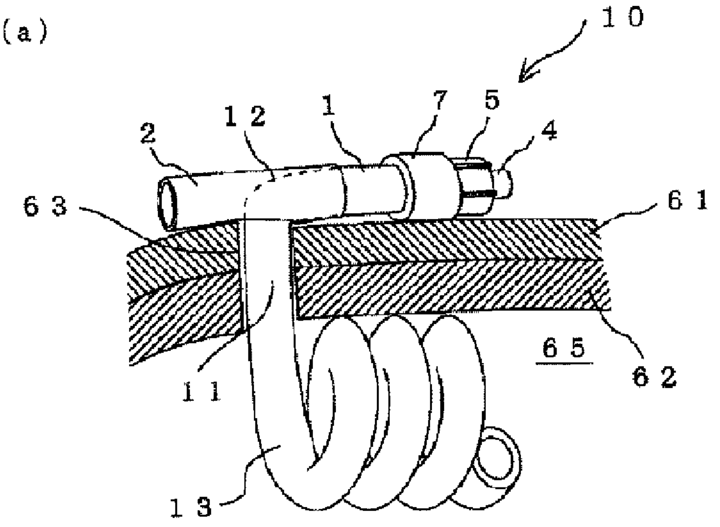
FIGS. 7*a*-7*b* show the situation when the fistula catheter according to Mode of Embodiment 1 is fitted in the fistula.
Figure 7:
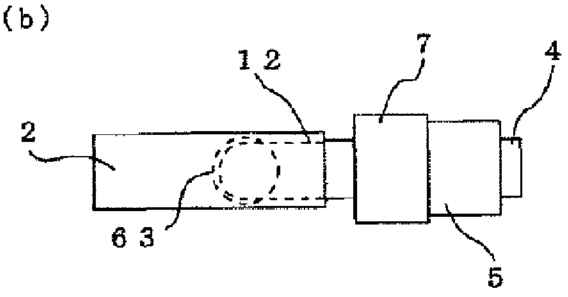

FIG. 7 shows the situation when the fistula catheter 10 is fitted in the patient's fistula 63, where FIG. 7(*a*) is a schematic side view and FIG. 7(*b*) is a view in which the patient's abdomen section is seen from the upper surface. The procedure for fitting the fistula catheter 10 having the above structure in the patient's fistula will be described with reference to FIGS. 6 and 7.

The fistula 63 is first of all formed in the patient's abdominal wall 61 and stomach wall 62, after which the extension tool 30 is assembled with the fistula catheter 10, whereby the situation shown in FIG. 6 is achieved. The fistula catheter 10 with which the extension tool 30 has been assembled is then positioned above the patient's abdominal wall 61, after which said fistula catheter is made to pass through the fistula 63 formed in the patient's abdominal wall 61 and stomach wall 62. At this point, the fistula catheter 10 is screwed in while being rotated together with the extension tool 30, and passes through the inside of the fistula 63. Once most of the body-internal fixing part 13 has entered the patient's stomach 65, the extension tool 30 is withdrawn from the fistula catheter 10.

As described above, when the fistula catheter 10 is fitted in the patient's fistula 63, the shape of the body-internal fixing part 13 reverts to its original helical shape which is long in the diametric direction and short in the axial direction. At this point, the section of the tube body 11 which is positioned inside the fistula 63 extends in a substantially linear fashion and the upper part of the helical body-internal fixing part 13 comes into contact with the inner surface of the stomach wall 62. As a result, the fistula catheter 10 is prevented from being withdrawn from the fistula 63 and is maintained in a fitted state in the patient's abdominal section. The opening at the tip end of the connector body 4 is then closed off with the cap 20. This completes the fitting of the fistula catheter 10 in the patient's body. This state is then maintained for 1 to 2 days. Bleeding from the fistula 63 stops during this time and the abdominal wall 61 and stomach wall 62 are fixed.

As shown in FIG. 7(*b*), the body-external fixing part 12 is linked in a substantially orthogonal direction with respect to the tube body 11, and therefore it is positioned so as to run along the surface of the patient's abdominal wall 61. Consequently, the fistula catheter 10 does not stand out, so the mental burden on patients concerned with appearance can be lightened. Furthermore, the short section which is exposed at the surface of the patient's body includes only the body-external fixing part 12 and the connector member 3, and therefore the fistula catheter 10 is unlikely to obstruct patient activity and self-removal can also be restricted.

When the patient ingests fluid such as liquid food or nutrients, the body-external fixing part 12 exposed from the fistula 63 in the abdominal wall 61 is pinched with the fingers etc. in order to block the flow path in the tube 1, and in this state the cap 20 is removed from the connector body 4 in order to connect the supply tube 50 to the connector body 4. When the flow path in the tube 1 is blocked by pinching with the fingers etc. in this way, it is possible to suppress return flow of fluid etc. inside the stomach 65 to outside the body through the tube 1. Furthermore, the tube 1 is made of a soft and flexible material, and therefore the patient or practitioner can easily press the tube 1 to block the flow path therein. Furthermore, the technique of pressing the tube 1 with the fingers etc. is simple and there is no need to use any special tools, and therefore the process is simple for the patient and practitioner, while the method of use is very easy to understand.

Figure 8:
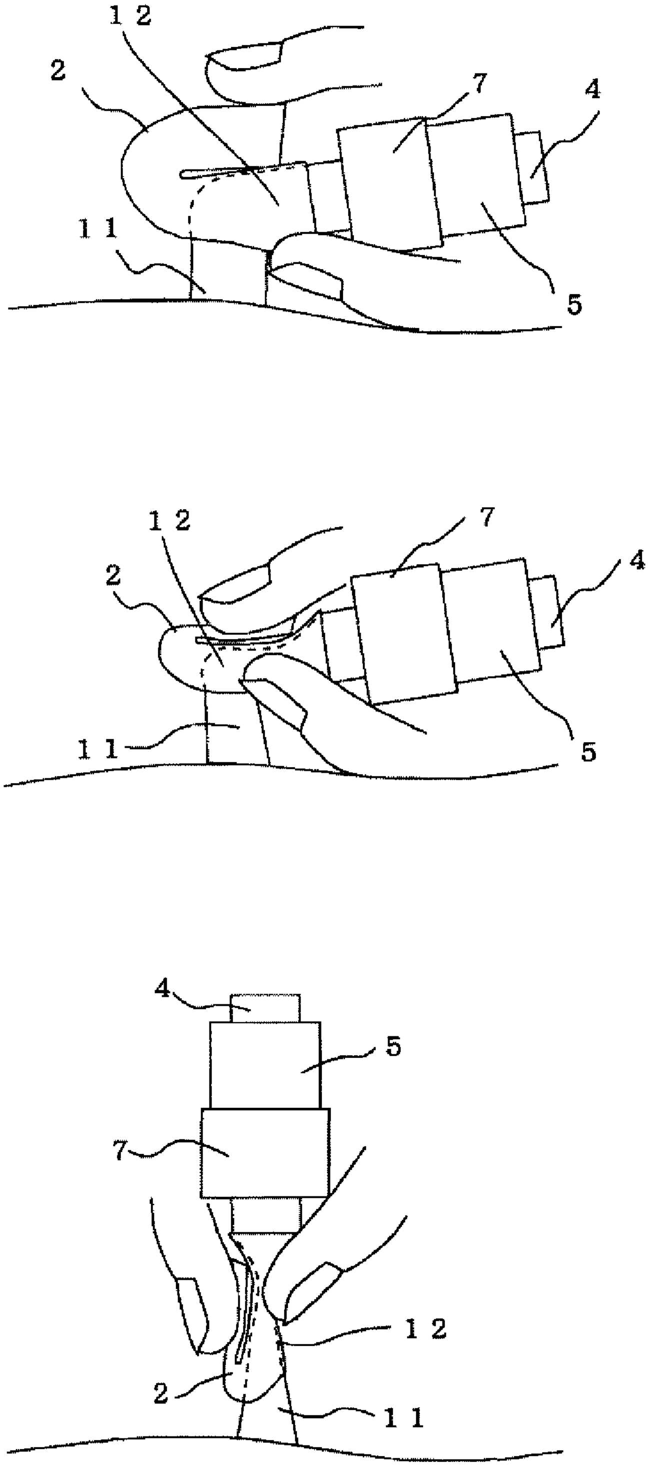
FIGS. 8*a*-8*c* illustrate the tube pressing operation employing the pulling-restriction member of the fistula catheter according to Mode of Embodiment 1.

Furthermore, in Mode of Embodiment 1, the pulling-restriction member 2 can be used to block the flow path in the tube 1. FIG. 8 illustrates the tube 1 pressing operation employing the pulling-restriction member 2.

As shown in FIG. 8(*a*) the patient or the practitioner folds the pulling-restriction member 2 in two and bends it towards the body-external fixing part 12. In Mode of Embodiment 1, the pulling-restriction member 2 includes a hollow tube which is soft and flexible, and therefore it can be easily bent.

As shown in FIG. 8(*b*), the pulling-restriction member 2 which has been folded in two is further pinched with the fingers in order to press the body-external fixing part 12. This makes it possible to block the flow path in the tube 1. The pulling-restriction member 2 and the body-external fixing part 12 are placed one over the other in order to increase the thickness of the section being pressed compared with when it is only the tube 1 which is pressed, and therefore it is simpler for the patient or practitioner to press the tube 1.

Furthermore, as shown in FIG. 8(*c*), the body-external fixing part 12 of the tube 1 may be stood upright and in this state the pulling-restriction member 2 may be placed on top and the tube 1 pressed. The tube body 11 and the body-external fixing part 12 are formed by bending the soft and flexible tube 1, and therefore the patient or practitioner can easily stand the body-external fixing part 12 upright. The issue of whether the body-external fixing part 12 is pressed while horizontal (while lying along the body surface) as shown in FIG. 8(*b*), or whether the body-external fixing part 12 is pressed while upright as shown in FIG. 8(*c*) is something which the patient or practitioner is free to select depending on which is simpler to perform.

While the flow path in the tube 1 is blocked in this way, the connector 52 (FIG. 4) of the supply tube 50 is connected to the connector body 4. Specifically, the tip-end opening of the connector body 4 and the tip-end opening of the connector 52 of the supply tube 50 are first of all placed facing each other and then brought close together. The cylindrical connecting part of the connector 52 is then inserted into the internal cavity 4*a* of the connector body 4, and the lock ring 5 is turned. By doing so, the female thread 5*b* formed on the inner peripheral surface of the lock ring 5 and the male thread (not depicted) formed on the connector 52 are screwed together.

Once the female thread 5*b* of the lock ring 5 and the male thread of the connector 52 have been suitably screwed together, the connector body 4 and the connector 52 are joined in a liquid-tight manner. By this means, the connector body 4 of the fistula catheter 10 and the connector 52 of the supply tube 50 are placed in communication and suitably linked so that there is no leakage of liquid.

In this state, fluid is introduced into the supply tube 50 from the tip-end opening of the supply tube 50. As a result, the fluid passes from the supply tube 50 through the internal cavities of the connector body 4, body-external fixing part 12, tube body 11 and body-internal fixing part 13 and is supplied into the patient's stomach 65. Furthermore, once the fluid has been ingested, the supply tube 50 is detached from the connector body 4 and the tip-end opening of the connector body 4 is closed. The cylindrical member 7 which has a larger diameter than the outer diameter of the lock ring 5 and is provided adjacent to the lock ring 5 and substantially coaxially therewith is provided so that when the supply tube 50 or the cap 20 is connected to the fistula catheter 10, it is possible to prevent release of the connection between the connector body 4 and the cap 20 or connector 52 due to the lock ring 5 being inadvertently turned. That is to say, the cylindrical member 7 obstructs turning of the lock ring 5, and therefore it is difficult for the patient or practitioner to access the lock ring 5 unless they intentionally try to access the lock ring 5. This means that it is possible to prevent the cap 20 or connector 52 becoming detached from the connector body 4 due to the lock ring 5 being inadvertently turned. It should be noted that in Mode of Embodiment 1 a cylindrical member 53 having the same structure as the cylindrical member 7 is provided on the connector 52 of the supply tube 50 (see FIG. 4).

As described above, in the fistula catheter 10 according to Mode of Embodiment 1, the body-external fixing part 12 is formed by the tube 1, and the body-external fixing part 12 is connected substantially at right-angles to the tube body 11 which is inserted into the fistula. This means that when the fistula catheter 10 is fitted in the fistula, the body-external fixing part 12 is positioned running along the body surface. The body-external fixing part 12 is therefore unlikely to obstruct patient activity, and it can be easily connected to the supply tube 50 for supplying nutrients etc. Furthermore, the body-external fixing part 12 is formed by the tube 1, and therefore it is unlikely to cause the patient pain and is only slightly invasive. In this way, the small body-external fixing part 12 has a simple external appearance when it is fitted, and is unlikely to obstruct patient activity such as changing clothes, and self-removal can also be restricted. Furthermore, the section which is exposed at the body surface is only small, and therefore the fistula catheter 10 does not stand out or look unattractive, so the mental burden on patients concerned with appearance can be lightened.

Furthermore, the body-external fixing part 12 is formed by the tube 1, and therefore the supply tube 50 can be easily attached thereto and detached therefrom. That is to say, when the supply tube 50 is attached or detached, the body-external fixing part 12 which is positioned running along the body surface is pinched and operations can be carried out with the body-external fixing part 12 raised to an upright position. In this way, the body-external fixing part 12 is positioned along the body surface but it is not fixed to the body surface, as is the case with what are known as button-type body-external fixing parts, and therefore the supply tube 50 can be attached or detached at a prescribed distance from the body surface, which makes the operation simpler.

Furthermore, the body-external fixing part 12 is formed by the flexible tube 1 and therefore when the supply tube 50 is connected to the fistula catheter 10, it is possible to block the flow path by pressing the tube 1, and this makes it possible to prevent return flow of fluid etc. from inside the alimentary canal. In this way, the flow path in the tube 1 can be blocked by the simple operation of pinching and pressing the tube 1, and therefore the patient and practitioner can readily understand how to use the system, and the ease of use is improved. Furthermore, there is no need to provide a structure such as a check valve inside the tube 1, so the number of components can be reduced. Furthermore, since there is no need to provide a check valve inside the tube 1, the size of the body-external fixing part 12 is not increased and the tube body 11 and body-external fixing part 12 can be provided with the same diameter.

Furthermore, the body-external fixing part 12 is connected substantially at right-angles to the tube body 11, and therefore it is possible to restrict pulling-in of the fistula catheter 10 into the fistula when the fistula catheter 10 is fitted in the fistula.

Furthermore, the pulling-restriction member 2 is provided extending in a different direction to the direction of connection of the body-external fixing part 12 with respect to the axial direction of the tube body 11. It is therefore possible to further restrict pulling-in of the fistula catheter 10 into the fistula when the fistula catheter 10 is fitted in the fistula. Furthermore, the pulling-restriction member 2 is formed by a flexible tube member, and therefore it is possible to pinch the pulling-restriction member 2 and the body-external fixing part 12 while one is on top of the other, so it is simple to press the tube 1 when the flow path in the tube 1 is to be blocked.

Furthermore, the tube body 11 and the body-external fixing part 12 are formed as a single piece by one tube, namely the tube 1, and therefore it is possible to reduce the number of components, which leads to reduced production costs. In addition, in Mode of Embodiment 1, the body-internal fixing part 13 is also formed by the tube 1 as a single piece with the tube body 11 and the body-external fixing part 12, and therefore there is a greater advantage in terms of reducing the number of components.

Furthermore, the connector member 3 which can be connected to the supply tube 50 is provided at the end of the body-external fixing part 12 on the opposite side to the end that connects to the tube body 11. This means that the fistula catheter 10 can be used as what is known as a button-type fistula catheter when the supply tube 50 is not connected, while it can also be used as what is known as a tube-type fistula catheter in which a long tube is exposed on the body surface side by connecting the supply tube 50 to the connector member 3. In this case too the body-external fixing part 12 is connected substantially at right-angles to the tube body 11, as described above, and therefore the tube 1 does not protrude upwards around the exit of the fistula and so is unlikely to obstruct patient activity.

Furthermore, in Mode of Embodiment 1, the body-internal fixing part 13 is produced by forming the lower part of the tube 1 into a helical shape. Consequently, when the fistula catheter 10 is fitted in the fistula, the abdominal wall 61 and the stomach wall 62 are held in a preferred positional relationship by the body-external fixing part 12 and the section of the body-internal fixing part 13 which is maintained in a helical shape.

At this point, the body-internal fixing part 13 expands or contracts according to the patient's body size and the positional relationship between the abdominal wall 61 and the stomach wall 62, and therefore it is possible to use one size of fistula catheter 10 for all patients. Furthermore, it is possible to provide some margin in the length between the tube body 11 and the section of the body-internal fixing part 13 which is positioned on the inner surface of the stomach wall 62 with respect to the length of the fistula 63, and therefore it is possible to prevent ulceration, and there is also no need to replace the fistula catheter 10 even if the patient's state changes when the fistula catheter 10 is indwelling in the patient's fistula 63. Furthermore, when the body-internal fixing part 13 is extended from a helical shape to a substantially linear shape, the axial length thereof increases, and therefore the fistula catheter 10 does not become detached from the patient's body.

Furthermore, the fistula catheter 10 according to Mode of Embodiment 1 is provided with the cylindrical member 7 which has a larger diameter than the outer diameter of the lock ring 5 and is provided adjacent to the lock ring 5 and substantially coaxially therewith. The cylindrical member 7 therefore obstructs access to the lock ring 5. This means that it is difficult for the patient or practitioner to access the lock ring 5 unless they intentionally try to access the lock ring 5. Thus, it is possible to prevent release of the connection between the connector body 4 and the cap 20 or supply tube 50 due to the lock ring 5 being inadvertently turned.

It should be noted that the connector member 3 of the fistula catheter 10 is not limited to what has been described in this mode of embodiment, and it is equally possible to use any connecting structure which allows attachment and detachment of the supply tube 50.

Mode of Embodiment 2

Figure 9:
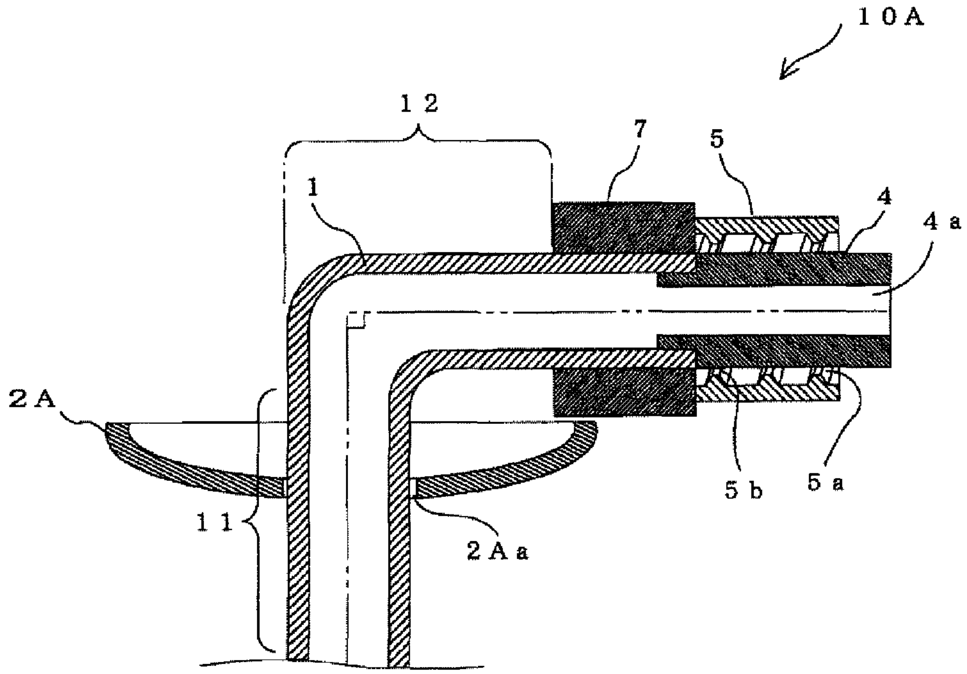
FIG. 9 is a schematic view in cross section of the main parts of the fistula catheter according to Mode of Embodiment 2.
Figure 10:
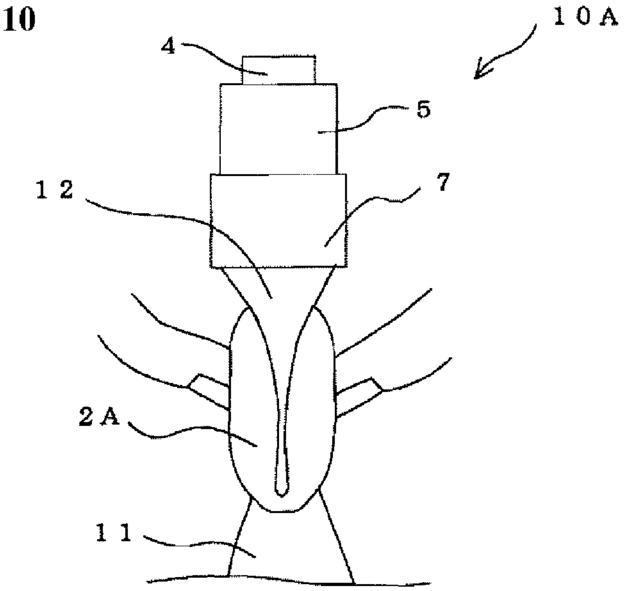
FIG. 10 illustrates the tube pressing operation employing the pulling-restriction member of the fistula catheter according to Mode of Embodiment 2.

In Mode of Embodiment 2, another exemplary structure for the pulling-restriction member will be described. FIG. 9 is a schematic view in cross section of a fistula catheter 10A according to Mode of Embodiment 2, and FIG. 10 illustrates the tube pressing operation employing the pulling-restriction member of the fistula catheter 10A according to Mode of Embodiment 2. It should be noted that the descriptions of Mode of Embodiment 2 and subsequent modes of embodiment will focus on differences with Mode of Embodiment 1 and components which are the same as or correspond to those of Mode of Embodiment 1 bear the same reference symbols.

The pulling-restriction member 2A according to Mode of Embodiment 2 includes a member having an elliptical dish-like outer shape and made of a soft and flexible material. The tube body 11 of the tube 1 is inserted into the pulling-restriction member 2A through a hole 2Aa provided in a substantially central position of the dish-like member which is thereby attached to the tube body 11. In FIG. 9, one of the semi-major axes of the elliptical pulling-restriction member 2A extends in the axial direction of the body-external fixing part 12, while the other semi-major axis thereof is disposed so as to face the opposite direction to the axial direction of the body-external fixing part 12. It should be noted that the pulling-restriction member 2A is rotatable in the circumferential direction of the tube body 11. Furthermore, the pulling-restriction member 2A is mobile in the axial direction of the tube body 11 and can also move to the position of the body-external fixing part 12; when the pulling-restriction member 2A is arranged in the manner shown in FIG. 9, the pulling-restriction member 2A does not project by a large amount from the surface of the patient's body, so it does not form a bulge under any clothes that the patient might be wearing, and there is unlikely to be any interference with the patient's daily life.

When the flow passage in the tube 1 is blocked using the pulling-restriction member 2A, as shown in FIG. 10, the body-external fixing part 12 of the tube 1 is raised upright, the pulling-restriction member 2A is folded in two, and the tube body 11 or body-external fixing part 12 is gripped and pinched so that the tube 1 is pressed. This makes it possible to block the flow path in the tube 1. When the pulling-restriction member 2A and the tube 1 are positioned one over the other, the thickness of the section being pressed is greater than when only the tube 1 is pressed, and therefore it is simpler for the patient or practitioner to press the tube 1.

The fistula catheter 10A comprising this kind of pulling-restriction member 2A can demonstrate the same advantages as in Mode of Embodiment 1. Furthermore, the pulling-restriction member 2A includes a dish-like member, and therefore when the tube 1 is pinched with the fingers in order to block the flow path, the concave part of the pulling-restriction member 2A forms a dish for accommodating the patient's fingers. This means that the fingers will not be readily separated from the pulling-restriction member 2A, and it is simple for the patient or practitioner to press the pulling-restriction member 2A regardless of their posture.

Mode of Embodiment 3

Figure 11:
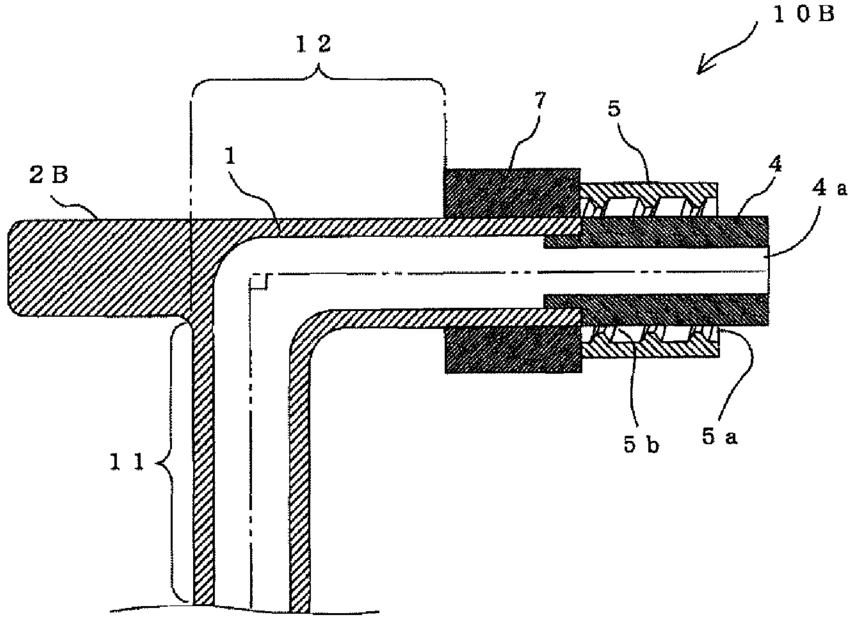
FIG. 11 is a schematic view in cross section of the main parts of the fistula catheter according to Mode of Embodiment 3.

In Mode of Embodiment 3, another exemplary structure for the pulling-restriction member will be described. FIG. 11 is a schematic view in cross section of a fistula catheter 10B according to Mode of Embodiment 3.

The pulling-restriction member 2B according to Mode of Embodiment 3 is formed to project in the opposite direction to the connection direction of the body-external fixing part 12 with respect to the tube body 11, in the same way as in Mode of Embodiment 1, but unlike in Mode of Embodiment 1, the pulling-restriction member 2B is formed by increasing the thickness of the peripheral wall of the tube 1. The pulling-restriction member 2B is formed as part of the flexible tube 1, and therefore the flow path in the tube 1 can be blocked using the same operation as that shown in FIG. 8.

The fistula catheter 10B comprising this kind of pulling-restriction member 2B can demonstrate the same advantages as in Mode of Embodiment 1. Furthermore, the pulling-restriction member 2B is formed by increasing the thickness of the peripheral wall of the tube 1, and therefore the tube body 11, body-external fixing part 12, body-internal fixing part 13 and pulling-restriction member 2B can be formed by a single tube, which contributes to reducing the number of components and reducing assembly costs.

Mode of Embodiment 4

In Mode of Embodiment 4, another exemplary structure for the body-internal fixing part will be described.

Figure 12:
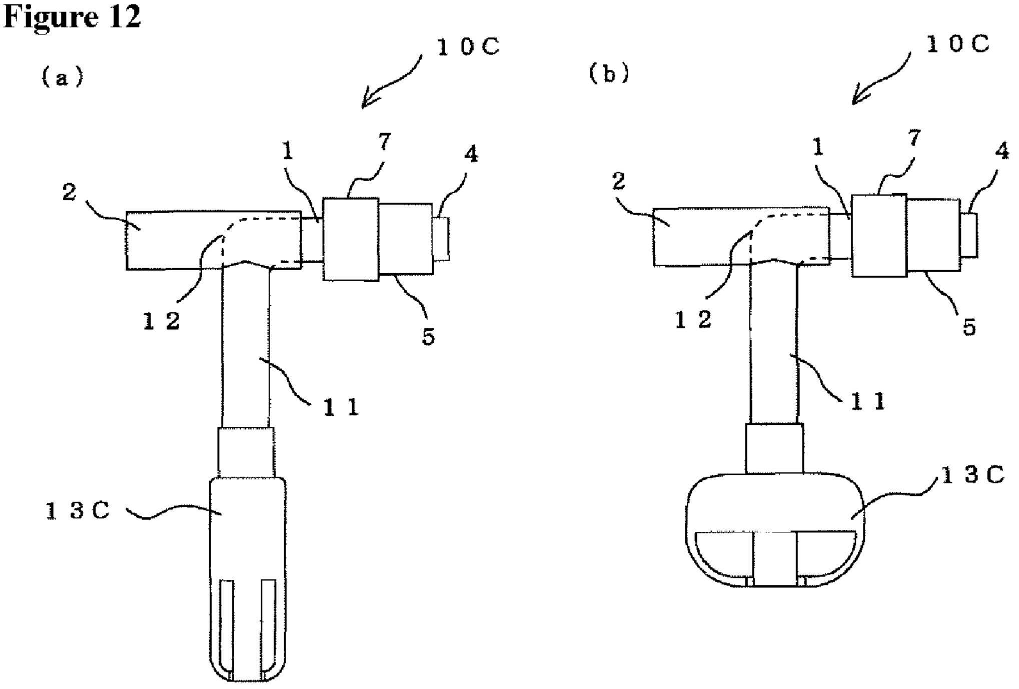
FIGS. 12*a*-12*b* are front views of the fistula catheter according to Mode of Embodiment 4.

FIG. 12 is a front view of the fistula catheter 10C according to Mode of Embodiment 4. The fistula catheter 10C shown in FIG. 12 is what is known as a bumper-type fistula catheter. The fistula catheter 10C is provided with a hemispherical body-internal fixing part 13C which grows larger in diameter towards the inside of the stomach wall, rather than the helical stomach-internal fixing part 13 described in Mode of Embodiment 1. When the fistula catheter 10C is inserted into the fistula, the body-internal fixing part 13C is contracted, as shown in FIG. 12(*a*), and then the body-internal fixing part 13C is expanded inside the stomach, as shown in FIG. 12(*b*). By doing so, the abdominal wall and the wall of the alimentary canal are held by the body-internal fixing part 13C and the body-external fixing part 12. The rest of the structure is the same as in Mode of Embodiment 1.

Furthermore, FIG. 13 is a front view of a fistula catheter 10D according to Mode of Embodiment 4. The fistula catheter 10D shown in FIG. 13 is what is known as a balloon-type fistula catheter. The fistula catheter 10D is provided with a body-internal fixing part 13D comprising an expandable balloon, rather than the helical stomach-internal fixing part 13 described in Mode of Embodiment 1. When the fistula catheter 10D is inserted into the fistula, the body-internal fixing part 13D is contracted, as shown in FIG. 13(*a*), and then the body-internal fixing part 13D is expanded inside the stomach, as shown in FIG. 13(*b*). By doing so, the abdominal wall and the wall of the alimentary canal are held by the body-internal fixing part 13D and the body-external fixing part 12. The rest of the structure is the same as in Mode of Embodiment 1.

As described above, what are known as bumper-type and balloon-type body-internal fixing parts may also be used, and the same advantages as in Mode of Embodiment 1 can be achieved. Furthermore, the specific structures of the bumper-type body-internal fixing part 13C and the balloon-type body-internal fixing part 13D are not limited to what is shown in FIGS. 12 and 13, and any structure may be adopted.

It should be noted that Modes of Embodiment 1 to 4 described above may be suitably combined. Furthermore, no particular limitation is imposed in terms of the shape of the body-internal fixing part, and any structure may be used aside from the structures described in relation to Modes of Embodiment 1, 3 and 4.

What is claimed is:

1. A fistula catheter comprising:

a tube body insertable into a fistula formed in an abdominal wall and a wall of the alimentary canal, the tube body extending in an axial direction;

a body-external fixing member which is linked to one end of the tube body, and positionable on an abdominal wall surface side of the fistula; and a body-internal fixing member which is linked to the other end of the tube body, and positionable against an inside wall of the alimentary canal;

wherein the body-external fixing member and the body-internal fixing member are respectively securable to the abdominal wall and the wall of the alimentary canal, and wherein the fistula catheter has a flow path allowing fluid to flow through the body-external and body internal fixing members, and is characterized in that:

the body-external fixing member comprises a flexible tube member that is connected substantially at a right-angle to the axial direction of the tube body; and a pulling-restriction member which extends in a direction opposite to the direction of connection of the body-external fixing member to the tube body and is provided on at least part of the tube body and the body-external fixing member, wherein the pulling-restriction member and the body-external fixing member in combination with the tube body define an overall T-shape with the flexible tube member connected at substantially the right-angle to the axial direction of the tube body.

2. The fistula catheter according to claim 1, characterized in that a connector for detachably connecting a fluid supply tube which supplies fluid is provided at one end of the body-external fixing member on a side opposite to an end of the body-external fixing member which is connected to the tube body.

3. The fistula catheter according to claim 2, characterized in that the connector comprises:

a lock ring including an outer diameter, an inner peripheral surface and a thread part located on the inner peripheral surface, the thread part configured to screw together with a thread provided on the fluid supply tube; and a cylindrical member which has a larger diameter than the outer diameter of the lock ring and is provided adjacent to the lock ring and substantially coaxially with the lock ring.

4. The fistula catheter according to claim 1, characterized in that the pulling-restriction member includes a flexible member which can be placed over the body-external fixing member by being bent.

5. The fistula catheter of claim 1, wherein the body-internal fixing member comprises one of a tube with a helical shape, an expandable hemispherical member, and an expandable balloon.

6. The fistula catheter of claim 1, wherein the pulling-restriction member is comprised of a bendable tube secured to the body-external fixing member.

7. The fistula catheter according to claim 1, wherein the body-external fixing member and the tube body are formed by a single tube member.

* * * * *